US011191515B1

(12) United States Patent
Vija et al.

(10) Patent No.: US 11,191,515 B1
(45) Date of Patent: Dec. 7, 2021

(54) INTERNAL DOSE ASSESSMENT WITH PORTABLE SINGLE PHOTON EMISSION COMPUTED TOMOGRAPHY

(71) Applicant: Siemens Medical Solutions USA, Inc., Malvern, PA (US)

(72) Inventors: Alexander Hans Vija, Evanston, IL (US); Francesc dAssis Massanes Basi, Chicago, IL (US); Miesher Rodrigues, Buffalo Grove, IL (US)

(73) Assignee: Siemens Medical Solutions USA, Inc, Malvern, PA (US)

( * ) Notice: Subject to any disclaimer, the term of this patent is extended or adjusted under 35 U.S.C. 154(b) by 0 days.

(21) Appl. No.: 16/949,298

(22) Filed: Oct. 23, 2020

(51) Int. Cl.
*A61B 6/00* (2006.01)
*A61B 6/03* (2006.01)
*A61B 6/04* (2006.01)

(52) U.S. Cl.
CPC .............. *A61B 6/542* (2013.01); *A61B 6/037* (2013.01); *A61B 6/0407* (2013.01); *A61B 6/4405* (2013.01); *A61B 6/5205* (2013.01); *A61B 2562/0219* (2013.01)

(58) Field of Classification Search
CPC .............. A61B 66/542; A61B 66/0407; A61B 66/5205; A61B 66/4405; A61B 66/037
See application file for complete search history.

(56) References Cited

U.S. PATENT DOCUMENTS

2019/0168029 A1 6/2019 Cachovan
2021/0106302 A1* 4/2021 Vija .................... A61B 6/4208
2021/0106848 A1* 4/2021 Vija .................... A61N 5/1039

OTHER PUBLICATIONS

Ljungberg, Michael, et al. “A 3-dimensional absorbed dose calculation method based on quantitative SPECT for radionuclide therapy: evaluation for 131I using Monte Carlo simulation.” Journal of Nuclear Medicine 43.8 (2002): 1101-1109.
U.S. Appl. No. 16/801,343, filed Feb. 26, 2020.
“Smartphone Radiation Detector App Tests Positive” https://phys.org/news/2014-06-smartphone-detector-app-positive.html Jun. 30, 2014.

* cited by examiner

*Primary Examiner* — Michael C Bryant

(57) ABSTRACT

For SPECT-based internal dose estimation, a portable detector is used to sample activity. The portable detector may selectively use far-field or near-field imaging for a SPECT scan. A camera and/or gyroscope assist in determining emission location and/or aligning activities from the different times. The time-activity curve or another dose is estimated using activities from different times where the activity for at least one time is from the portable detector, which may allow for more frequent sampling of activity and more accurate dose estimation.

20 Claims, 3 Drawing Sheets

INTERNAL DOSE ASSESSMENT WITH PORTABLE SINGLE PHOTON EMISSION COMPUTED TOMOGRAPHY

BACKGROUND

The present embodiments relate to single photon emission computed tomography (SPECT). SPECT systems are standalone machines, which are usually fixed in place in a dedicated room. In SPECT, gamma camera detectors are planar detectors with about 2000 $cm^2$ area and are designed to allow the imaging of clinically relevant features without or only minimal patient truncation (e.g., a 40×50 $cm^2$ detector to axially cover at least both kidneys and image most of a patient torso). This size, including dedicating a room to one imaging system, may be costly. Patients are inconveniently brought to the imaging system, which is fixed in place. Some medical scanners have been positioned in a truck so that hospitals without a dedicated tomography imaging system may have access to such a system. The patient is brought to the truck and placed in the imaging system fixed in place in the truck.

The energy deposition administered to the patient is assessed with image-based dosimetry. Dosimetry allows adaptation of the therapeutic dose to a higher limit without adverse effect to healthy tissue, improving outcome, or allows limiting side effects. Patients without dosimetry adaptation may be undertreated.

For dosimetry, the time activity curve or dose is computed from tomographic quantitative images of the activity at various time points. The truck-based or room-based large, single devices do not allow for convenient determination of activity at times spaced apart by hours or days in dose estimation. The number of scans of the patient may be limited (e.g., up to 5-6 scans) and require up to 120 hours of patient hospitalization. Most hospitals only perform one scan. The accuracy of the dosimetry is thus a logistical problem, as measurements at a desired number of the time points to capture the complicated dynamics of various therapeutic agents may not be provided.

Portable, solid-state devices from homeland security applications may use nonadaptive coded aperture image formation to image a patient. The patient is far from the device, satisfying the far-field approximation, as the approach is derived from security applications whereby one attempts to discover radioactive source in open or closed space from a far distance. This may not provide sufficient information and/or is unduly limiting in the imaging requirements.

SUMMARY

By way of introduction, the preferred embodiments described below include methods, computer readable storage media, and systems for SPECT-based internal dose estimation. A portable detector is used to sample activity. The portable detector may selectively use far-field or near-field imaging for a SPECT scan. A camera and/or gyroscope assist in determining emission location and/or aligning activities from the different times. The time-activity curve or dose is estimated using activities from different times where the activity for at least one time is from the portable detector, which may allow for more frequent sampling of activity and more accurate dose estimation.

In a first aspect, a single photon emission computed tomography (SPECT) system includes a handheld scanner having a solid-state detector configured to detect emissions from a patient and an imager configured to image the patient. An image processor is configured to determine internal dose from a time activity curve formed from activities of different scans at different times. The activities are tomographically formed from (1) emissions detected from the patient by the solid-state detector during the different scans of the different times and (2) output of the imager. The image processor is configurable to tomographically form the activities with the patient in a far-field of the solid-state detector or a near-field of the solid-state detector.

In one embodiment, the imager is a camera. The optical images output of the camera may be used in one or more ways for tomographically forming the activities. For example, the image processor is configured to form the activities where a position or positions of the handheld scanner are determined from the output of the camera. As another example, the image processor is configured to form the activities as multi-modal reconstructions with the output of the camera being images used to estimate internal structure of the patient for the multi-modal reconstructions. In another example, the image processor is configured to form the activities where a position or positions of the patent at the different times are determined from the output of the camera. The time activity curve is determined with the activities of the different times aligned with the output of the camera.

In another embodiment, the image processor is configured to determine the dose by fitting the time activity curve to the activities of the different times. For example, the image processor is configured to determine the dose by fitting the time activity curve to the activities of the different times and an activity of an additional time. The activity of the additional time is from a SPECT scanner having a bed onto which the patient is placed for scanning.

The handheld scanner may be carriable by a person. For example, the handheld scanner weighs 5 kilograms or less. For scanning, the handheld scanner may be mounted to a stand. In one embodiment, the handheld scanner further includes a gyroscope. The image processor is configured to form the activities using orientations from the gyroscope.

In one embodiment, the solid-state detector is configured to detect at different energies. The image processor is configurable to tomographically form using a collimator for a lower one of the different energies and using Compton imaging for a higher one of the different energies.

The detector is usable with either far-field or near-field approximation. For far-field, the patient is within a subtended angle of the solid-state detector that encompasses the patient such that the activity is formed with the handheld scanner in one position. For near-field, the patient is closer to the handheld scanner wherein the subtended angle covers only a portion of the patient such that the activity is formed with the handheld scanner being moved to sense from different positions relative to the patient. In another example, the solid-state detector has a spatial resolution of 1 mm or less and is less than 500 square centimeters. Far-field is a distance from the patient to the handheld scanner of at least 1 meter.

In a second aspect, a method is provided for internal dose assessment in SPECT. A first activity distribution in a patient is determined with a first SPECT scan of the patient on a bed of a SPECT scanner. The first activity distribution represents the patient at a first period. A second activity distribution in the patient is determined with a second SPECT scan of the patient using a person-carriable detector. The second activity distribution represents the patient at a second period. The internal dose to the patient is estimated from the first and second activity distributions.

In one embodiment, the first activity distribution is determined by reconstructing the first activity distribution from the first SPECT scan as a multi-modality scan using computed tomography. The second activity distribution is determined by reconstructing the second activity distribution at a lower spatial resolution than the first activity distribution. In other embodiments using near-field approximation, the second activity distribution is determined by detection of emissions using the person-carriable detector being positioned at different orientations relative to the patient. A camera and/or gyroscope of the person-carriable detector is used to align the emissions with the patient.

The internal dose is estimated, in one embodiment, by fitting a time activity curve to activities of the first and second activity distributions.

In one embodiment using far-field approximation, the second activity distribution is determined with a lesser depth resolution than lateral resolution, and the person-carriable detector is held in a single orientation relative to the patient during the second SPECT scan.

Where the detector is a solid-state device, the second activity distribution may be determined with emissions detected by the person-carriable detector at energies at or below 511 KeV and reconstruction relying on lines-of-response based, at least in part, on collimation. The second activity distribution may be determined with emissions detected by the person-carriable detector at energies at or above 511 KeV and reconstruction with Compton imaging.

In a third aspect, a method is provided for internal dose assessment in SPECT. A first activity distribution in a patient is determined with a first SPECT scan of the patient on a bed of a SPECT scanner. The first activity distribution represents the patient at a first period. Near-field or far-field scanning for a portable solid-state detector is selected, such as selecting based on a measured range or based on user input. A second activity distribution in the patient is determined with the portable solid-state detector using the selected near-field or far-field scanning. The internal dose to the patient is determined from the first and second activity distributions.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
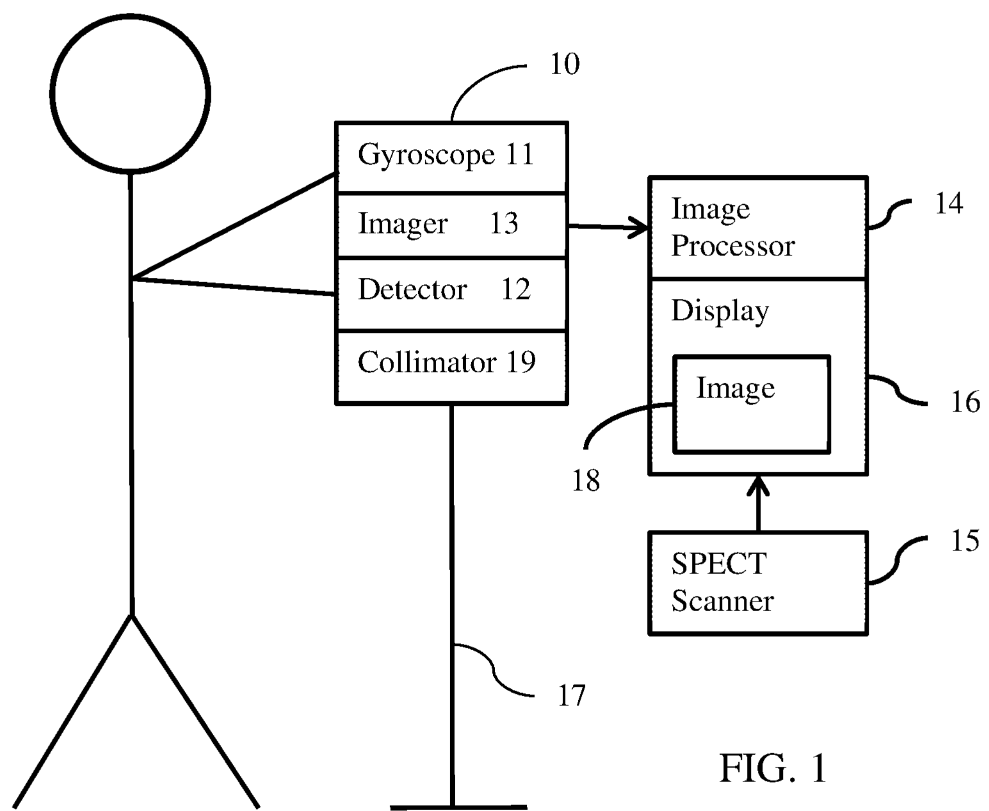
FIG. 1 is a SPECT imaging system using a portable detector according to one embodiment.

Internal dose is assessed, at least in part, using a portable quantitative minification SPECT with adaptive image formation. SPECT image formation is based on the Anger principle using a scintillation detector (e.g. NaI(TI)) and a lead (Pb) multi-channel collimator. Recent advances replace the detector with a direct converter, such as Cadmium zinc telluride (CZT) and/or the Pb with tungsten (W), yet the image formation process is not altered, still using a multi-channel collimator. The use of another collimated image formation, such as multiplexed or non-multiplexed multi-pinhole is reserved to dedicated organ imaging. For dosimetry, the entire body or at least the torso is to be measured. Image formation that allows for whole body imaging with a very small portable formfactor device is desired.

Besides fundamental technical energy propagation computation, the activity distribution is to be measured as often as possible, such as a fast scan and without much hassle to the imaging providers or patient. A small, portable solid-state detector module may be used as a handheld device that may scan while held or mounted to a mechanical support. The portable detector module is able to image a patient using an imager, such as an optical camera (stereoscopic, 4D time of flight (TOF), 3D structured light, laser scanner, optical tracker or Infrared) and image the patient using the detector, such as gamma-ray imaging with highly minifying adaptive image formation.

Minification is provided where the image size<the object size. Imaging at distance between 0.01 m to 10 m (near to far field) from the patient yields a corresponding subtended angle and attempts to resolve the activity distribution from less than 3 mm to 3 cm. For each scan, the data is continuously acquired, and the optical sensor (or other optional sensors) record the body movement for later registration with the reconstructed gamma-ray data to deliver a registered overlay of the activity distribution. As the system is small it can be hand-held or mounted in any small room, thus not requiring in-patient hospitalization, to monitor and record the patient activity and thus enable a temporal dataset with greater resolution. The patient is not required to be at a hospital for examination. The entire system may be mounted on a mobile platform (i.e., mobile cart, vehicle) or carried where the follow-up exams happen outside the hospital, or in some cases the entire image system goes to the patient's home for the follow-up examinations.

Adaptive image formation provides imaging over a wide range of energies<200 keV to <3000 keV where the image formation could change from physical collimation (i.e., multichannel or multiplexed) to electronic collimation using Compton imaging. In a hierarchical information gathering, activity is provided with image quality obtained with a dedicated large footprint scanners and a small portable system providing spot checks. By integrating into the handheld device solid-state detection of gamma rays using suitable image formation and imaging of other wavelengths (e.g., optical) to supply ancillary information (extra modal information) in one system, the device may be used to image a patient over an extend period of time. The accumulation and decay of the activity due to physical decay and biological re-distribution and excretion may be more accurately tracked due to convenience.

FIG. 1 shows one embodiment of SPECT system. The SPECT system implements the method of FIG. 3 or a different method. A handheld scanner 10 is used for dosimetry to provide additional sampling of activity and/or for operation using a selectable one of near-field and far-field imaging.

The SPECT system includes a handheld scanner 10, an image processor 14, a display 16, and a SPECT scanner 15. Additional, different, or fewer components may be provided.

For example, the SPECT scanner 15 is not provided. As another example, the display 16 is not provided, such as where estimates of the dose from the image processor 14 are used for applying additional radiopharmaceutical without imaging. In yet another example, user input devices (e.g., keyboard, touchscreen, touch pad, mouse, track ball, buttons, knobs, sliders, and/or rocker switches) are provided for user control of the handheld scanner 10, the image processor 14, and/or the SPECT scanner 15.

The handheld scanner 10 includes a gyroscope 11, imager 13, collimator 19, and detector 12. Additional, different, or fewer components may be provided. For example, an accelerometer, magnetic positioning sensors, and/or other position or orientation sensors are included. As another example, the gyroscope 11 and/or imager 13 are not provided. In yet another example, the collimator 19 is not provided, such as where Compton imaging is performed.

The handheld scanner 10 is sized to be carried by a person or pair of people. The handheld scanner 10 is held by hand or carriable between uses. The handheld scanner 10 is portable, such as being on a cart, in a bag, and/or having a form factor with one or more handles. During scanning, the handheld scanner 10 may be mounted to the mount 17 or continues to be carried by hand of a user.

In one embodiment, the handheld scanner 10 weighs 5 kilograms or less. For example, the handheld scanner 10 is 1-3 kilograms. Heavier or lighter embodiments may be provided. The handheld scanner 10 may be sized as a briefcase in size (e.g., 6×16×24 inches) or as a shoebox (e.g., 6×8×14 inches). Any size may be provided. The handheld scanner 10 is a small, portable solid-state detector module that can be used either as a handheld device or mounted to the mount 17 (e.g., a mechanical support). As the scanner 10 is small, the scanner 10 may be hand-held or mounted in any small room, thus not requiring in-patient hospitalization to monitor and record the patient activity. As the scanner 10 is small, the scanner 10 may not require any or may require fewer in-patient hospitalization to monitor and record the patient activity at different periods. The handheld scanner 10 enables a temporal dataset with higher resolution than relying on the large, fixed SPECT scanner 15 alone. The patient is not required to be at a hospital for any or all scans. The scanner 10 may be mounted on a mobile platform (i.e., mobile cart or vehicle) or carried where the follow-up exams happen outside the hospital or in some cases in the patient's home for the follow-up examinations.

The detector 12 is a detector configured to detect emissions from a patient. The detector 12 detects radiation from the patient. For example, emissions from radioactive decay are detected. Gamma radiation is detected.

The detector 12 is of any size based on weight and space limitations of the scanner 10. In one embodiment, the detector 12 is 10×10 cm, 5×5 cm, 3×5 cm or 5×7 cm, but other sizes may be used. Any shape, such as a flat or curved plate that is square, rectangular, or another shape, may be used. In one embodiment, the detector 12 ranges in size by area from less than 25 square cm to less than or equal to 500 square cm. Smaller or larger detectors 12 may be used.

The detector 12 is a solid-state detector, such as being a semiconductor. For example, a CZT or other direct conversion gamma ray detector is used. In one embodiment, a CdTe based (e.g., CdZnTe) with an ASIC for room-temperature semiconductors is used. Other high-Z room-temperature semiconductors may be used. Other solid-state detector modules include Si, CZT, CdTe, HPGe, TIBr, or similar devices. The detector 12 is created with wafer fabrication at any thickness, such as about 4 mm for CZT. Alternatively, the detector 12 is another type of sensor.

The detector 12 may include a semiconductor formatted for processing. For example, the detector 12 includes an application specific integrated circuit (ASIC) for sensing photon interaction with an electron in the detector 12. The ASIC is collocated with the pixels of the detector 12. The ASIC is of any thickness. A plurality of ASICs may be provided, such as 9 ASICS in a 3×3 grid of the detector 12.

The detector 12 may operate at any count rate. Electricity is generated by a pixel due to the interaction with radiation. This electricity is sensed by the ASIC. The location, time, and/or energy is sensed. The sensed signal may be conditioned, such as amplified, and sent to a transceiver for wireless communication.

The collimator 19 may be included in or by the detector 12. Any type of collimator 19 may be used, such as a multi-channel collimator, a multiplexed collimator, or a time-encoded multiplexed collimator. Alternatively, no collimator is provided, such as where electronic collimation is provided by Compton imaging.

The detector 12 may detect emissions at different energies. The same detector 12 is used for detecting emissions at any of the different energies or energy ranges. For example, the detector 12 is used for adaptive image formation where emissions as energy of less than 200 keV to less than 3000 keV may be detected. Alternatively, the detector 12 is designed for detecting energies at a specific energy range, such as around 511 keV. The image formation may be different for different energies, such as changing from physical collimation (e.g., multichannel or multiplexed) to electronic collimation using Compton imaging based on the energy range being imaged. For example, physical collimation by the collimator 19 is provided for energies at or less than 511 keV, less than 400 keV, or less than 600 keV. Electronic collimation is used for higher energies. In one embodiment, the detector 12 has an energy resolution of less than 1% at 662 keV.

The detector 12 has any spatial resolution, such as a spatial resolution of 1 mm or less. The detector 12 is used to perform gamma-ray imaging with minifying adaptive image formation. Minification is provided where the image size is less than the object size. For example, the scanner 10 is positioned at distance from the patient of between 0.01 m to 10 m (near to far-field), yielding a corresponding subtended angle and attempt to resolve the activity distribution from less than 3 mm to 3 cm. In this case, the object size is the size of the anatomy of interest. Larger spatial resolution than 1 mm may be provided. Image formation methods that minify include multi-channel collimation, multiplexed, time-encoded multiplexed, or intrinsic sensor Compton imaging.

For SPECT imaging, the location and orientation of the detector 12 relative to the patient is determined for locating the lines of response of detected emissions. The location and orientation of the detector relative to the patient may alternatively or additionally be used for motion correction, spatial registration of activity across time (e.g., tracking), estimating attenuations by location for reconstruction, and/or other uses. For example, the imager 13 may record the body movement or position for later registration with the reconstructed gamma-ray data to deliver a registered overlay of the activity distribution. The scanner includes the imager 13 and/or gyroscope 11 for determining the location and orientation of the detector 12 and/or patient.

The imager 12 is a scanner, such as a transmission-based scanner, to scan the patient. Any scanner, such as ultrasound, small enough to fit in the handheld scanner 10 may be used. In one embodiment, the imager 13 is an optical or infrared camera. The camera may determine depth information, such as a stereoscopic camera. A four-dimensional time of flight camera, a camera using structured light to estimate three-dimensional surface, a laser scanner, or optical tracker may be used.

The gyroscope 11 is a solid-state gyroscope. Other position and/or orientation sensors may be used, such as a range sensor, magnetic positioning sensor, accelerometer, and/or global positioning sensor. The gyroscope 11 and/or other sensor with the imager 13 enable precision location and orientation determination of the scanner 10 relative to the patient and/or environment. A stationary reference unit spaced from the scanner 10 may be used improve accuracy.

The scanner 10 communicates with the image processor 14. The image processor 14 may be integrated into or with the scanner 10. Alternatively, wired or wireless communication is provided between the scanner 10 and the image processor 14. The image processor 14 may be part of the SPECT scanner 15 or a separate workstation or server. The communications are used to transmit detected signals (e.g., emission or decay events) and/or position and orientation measurements. Alternatively, reconstructed activity distribution is transmitted. The transmissions are direct to a master device, such as the image processor 14 (e.g., computer, tablet, or workstation hosting the image processor 14).

The mount 17 may itself be portable. The mount 17 is a stand, tripod, or other structure for holding the scanner 10 in place during scanning. The mount is connectable with the scanner 10, such as using latches, snap fit, slider and pins, or another releasable connection. One or more motors may be included for moving the scanner 10 to scan from different locations relative to the patient in near-field imaging. The mount 17 may hold the scanner 10 in one position for far-field imaging. In alternative embodiments, the mount 17 is not provided. The user holds the scanner 10 to scan the patient.

The image processor 14 is a general processor, digital signal processor, application specific integrated circuit (ASIC), field programmable gate array, graphics processing unit, digital circuit, analog circuit, and/or another now known or later developed processor for performing tomography. The image processor 14 may be formed from multiple devices, such as an ASIC for detecting events and determining a line of response relative to the patient for each event, a general processor for tomographic reconstruction and dose estimation, and a graphics processing unit for rendering an image from the tomographically generated representation of the interior of the object. Parallel and/or serial processing may be used. The image processor 14 is configured by hardware, firmware, and/or software.

The image processor 14 is configured to generate an activity distribution with tomography. The counts and the positions on and of the detectors 12 relative to the patient (i.e., positions indicating the lines of response) are used to reconstruct a two or three-dimensional activity representation of the patient. For each scan, the activity distribution is tomographically formed from (1) emissions detected from the patient by the solid-state detector 12 and (2) output of the imager. Any know known or later developed reconstruction may be used. For example, physical collimation is used in image formation for energies below 400 keV and Compton imaging is used for reconstruction from emissions at energies above 400 keV. The collimator 19 may indicate the orientation of lines of response relative to the detector 12. Since the detector 12 detects emissions over a wide range of energies (e.g., <200 keV to <3000 keV), the image formation changes from physical collimation (i.e., multichannel or multiplexed) to electronic collimation using Compton imaging at a threshold energy (e.g., 400, 500, 510, 512, or 600 keV).

For reconstruction of the activity distribution for a period (i.e., time of a complete scan), the image processor 14 determines the lines of response for the measurements (e.g., emission occurrence with or without energy). The image processor 14 is configured to identify lines of response for the signals from the position and orientation information from the imager 13, gyroscope 11, and/or other sensor. Patient and/or detector 12 movement or position and orientation for each detected emission is determined and used to establish the line of response along which the emission occurred in the patient. A position or positions of the handheld scanner are determined from the output of the camera (i.e., optical images or depth images). The position of the patient relative to the detector is determined so that the line of response originating on the detector pixel sensing the emission is defined in position and orientation passing through the patient In one embodiment, the output of the imager 13 and/or gyroscope are used in multi-modal reconstruction. For example, a previous scan of the patient included a computer tomography (CT) scan. The patient position and orientation relative to the scanner 10 is used to align (e.g., morph) the CT data to be used for attenuation correction and/or structure/tissue specific reconstruction. The internal structure of the patient is estimated based on the output for multi-modal reconstruction. In another embodiment, the optical image with or without distance information is used to generate an estimate of CT data for the patient, which CT data is used in the multi-modal reconstruction.

In another embodiment, the patient and/or scanner 10 moves during the period of a given scan. The position and orientation information from the imager 13 and/or gyroscope 11 are used to determine the line of response for each detected emission. The line of responses relative to the patient during movement by the patient are determined.

In other embodiments, the position and/or orientation information are used to align reconstructed activities from different scans and corresponding periods. Combinations of the different embodiments may be used.

The image processor 14 is configured to tomographically reconstruct the two or three-dimensional representation of activity from the lines of response. Any tomographic reconstruction may be used. In an iterative process, such as using forward and backward projection from measurement space to object or image space, a spatial representation of the object is generated by optimization. The scanner 10 is represented as a system model used in the reconstruction. The image processor 14 determines a spatial distribution based on the signals and the system model. The spatial distribution is a two or three-dimensional distribution. A two or three-dimensional representation of activity in an internal region of a patient is generated by tomography from signals of the detectors 12. The locations of emissions are represented for SPECT.

Figure 2A:
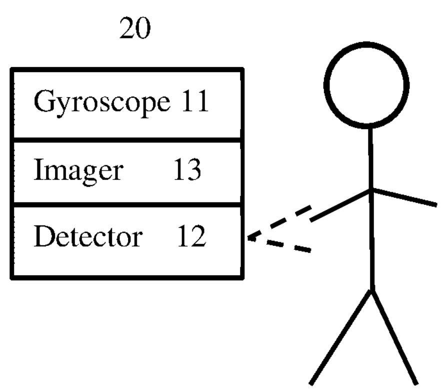
FIGS. 2A and 2B shows near-field and far-field use, respectively, of the portable detector.

The tomographic reconstruction may use near-field or far-field approximation. The same detector 12 and scanner 10 may be used for either far or near-field-based imaging. The activity distribution within the patient for a period or timepoint is determined tomographically based on near-field or far-field sensing of the detector. The patient is either in the near-field or the far-field of the field of view of the detector 12. FIG. 2A shows near-field sensing 20, such as where the subtended angle (shown by dashed lines) of sensitivity of the collimator 19 and/or detector 12 senses from only part of the patient or a sub-set of the part of the patient that is of interest. For example, the detector 12 and scanner 10 are within 1 meter of the patient. As a result, the near-field reconstruction uses emissions detected with the detector 12 at different positions and/or orientations relative to the patient. The detector 12 and scanner 10 are moved to detect emissions from different locations and/or orientations. To scan the entire patient and/or region of interest (e.g., torso), the detector 12 is moved to detect emissions from different regions at different times in the scan period. The detector 12 may also be moved to detect emissions from different orientations for the same locations.

Figure 2B:
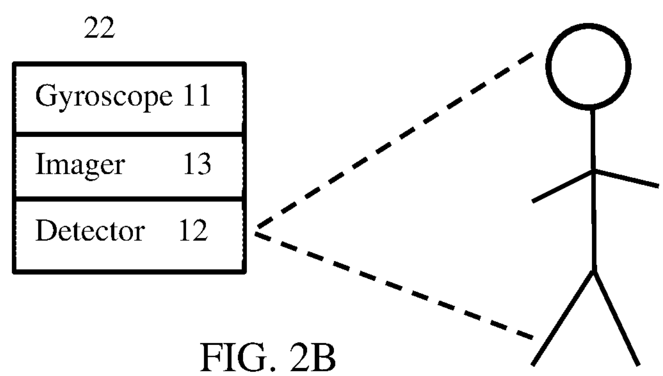

FIG. 2B shows far-field sensing 22, such as where the subtended angle of the detector 12 and/or collimator 19 senses emissions from the entire region of interest (e.g., entire patient or torso). The detector 12 may be held at one position and orientation relative to the patient. The resulting reconstructed activity distribution may have a lesser resolution in depth than laterally relative to the detector 12 due to using the single position and orientation to detect the emissions. The resolution may be increased by far-field sensing from different orientations.

Far and near-field may be distinguished by user entry identifying far or near-field. Alternatively, the imager 13 is used to sense the distance, such as using stereo cameras, time-of-flight, or other three-dimensional imaging. The image processor 14 is configured to reconstruction based on far-field or near-field sensing. The type of reconstruction and/or the available data for reconstruction is different for far-field verses near-field.

Referring to FIG. 1, the image processor 14 may be configured to generate an image 18 from the representation. Volume, surface, or other rendering may be performed for a three-dimensional representation. The three-dimensional distribution is rendered to a two-dimensional image 18 for display from a given viewing direction. Alternatively, a slice or plane represented in the three-dimensional representation is used to select data to form a two-dimensional image 18. For a two-dimensional distribution or representation, a two-dimensional image 18 is generated. The image of the activity distribution at a given period may be overlaid on an image from the imager 13 for the same or a different time.

The image processor 14 is configured to determine internal dose from a time activity curve formed from activities of different scans at different times. A time activity curve is fit to the activities of the different times. The fit time activity cure or characteristics thereof (e.g., integral under the curve) indicates the dose. The activities for a given location are aligned, such as with the images or data from the imager 13. The aligned activities for a location or continuous group of locations (e.g., for an organ or tissue region) as summed or averaged are used for curve fitting.

In one embodiment, the SPECT scanner 15 is a full-sized SPECT scanner. The SPECT scanner 15 is fixed to a floor of a dedicated room or truck. This SPECT scanner may include a CT imager for multi-modality reconstruction. The SPECT scanner 15 includes a bed dedicated to the scanner. The patient lies upon the bed for SPECT scanning. The resulting activity distribution may have a greater spatial resolution than using the detector 12. The activity over time of the patient may be sub-sampled or processed so that the curve fitting is fit to the activity distribution from the SPECT scanner 15 and one or more activity distributions reconstructed from scans by the detector 12 at different periods or times. Any combination of activity distributions from the detector 12 and the SPECT scanner 15 may be used. Any number of activity distributions from one or more (e.g., five or more, such as ten) different scans and corresponding periods may be used in fitting.

The display 16 is a CRT, LCD, projector, printer, or other display. The display 16 is configured to display the tomographic image 18 and/or an estimated dose (e.g., a dose value or the time activity curve). The dose and/or image 18 or images 18 are stored in a display plane buffer and read out to the display 16. The images 18 may be a sequence of images generated for different scans. The image 18 or images 18 are of the two or three-dimensional representation of activity in the internal region of the patient, so represent a view of the interior of the patient. Images representing an exterior view may be generated, such as a view from the imager 13. The dose may be displayed for modulating further dosing decisions.

Figure 3:
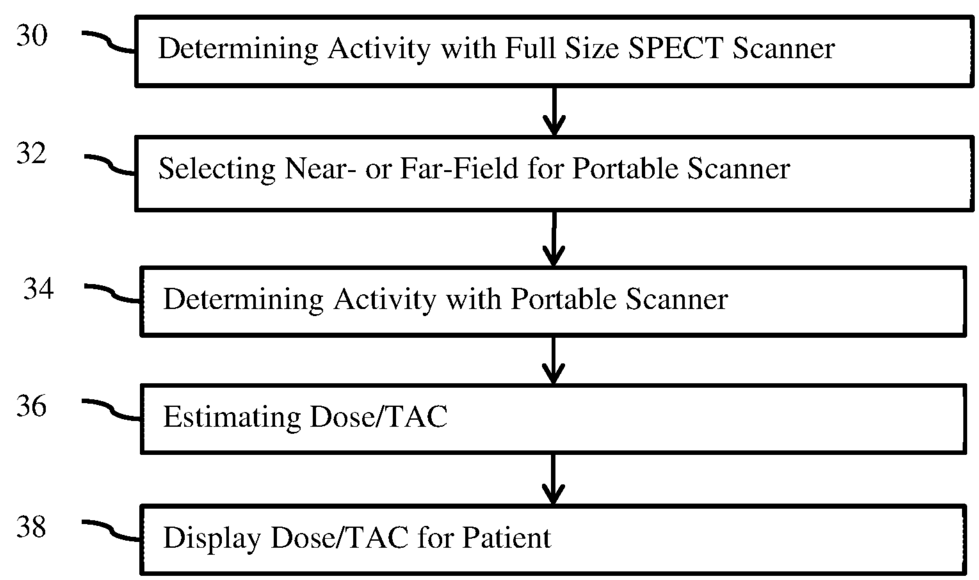
FIG. 3 is a flow chart diagram of one embodiment of a method for internal dose assessment in SPECT.

FIG. 3 shows one embodiment of a flow chart of a method for internal dose assessment in SPECT. The method uses hierarchical information gathering. A dedicated large footprint SPECT scanner is used to sample activity in a patient one or more times, such as when the patient first receives a radio pharmaceutical and any other times the patient is otherwise at the hospital or imaging suite or facility. A small portable SPECT scanner is used to provide spot checks to sample activity at one or more other times, such as the patient periodically visiting a pharmacy, scanning at home, or renting the portable SPECT scanner. Using the portable SPECT scanner, the imaging is less of a hassle, which allows for extra temporal sampling of the patient's activity distribution.

The method may be implemented by the system of FIG. 1 or another arrangement. The SPECT scanner 15 performs act 30. The portable scanner 10 performs act 34. An image processor and/or user input performs acts 32 and 36. The image processor may perform parts of acts 30 and 34, such as estimating lines of response and reconstructing from detected emissions. The display 16 is used for act 38. Other systems or devices may be used.

The acts are performed in the order shown (i.e., top to bottom or numerically) or other orders. For example, acts 30, 32, and 34 are performed in any order. Act 30 and/or acts 32 and 34 may be repeated any number of times.

Additional, different, or fewer acts may be provided. For example, act 32 is not performed. As another example, act 38 is not performed, such as where the estimated dose is used in dosimetry without displaying an image. In yet another example, acts for user input and control are provided. In another example, act 30 is not performed. Instead, the portable scanner is used for all sampling of the activity.

In act 30, the full-sized SPECT scanner and/or image processor determines an activity distribution in a patient with a SPECT scan of the patient on a bed of the SPECT scanner. The SPECT scan may include a CT scan for multi-modal reconstruction. The activity distribution in a region of interest of the patient or for the entire patient is determined. The scan occurs over a period as emissions are detected. These emissions are used to reconstruct the activity distribution, providing the activity in the patient at a given timepoint.

The activity distribution is determined from detected emissions. The detector senses radiation (e.g., gamma radiation) from the patient. For example, the patient ingests or is injected with a radiopharmaceutical. Emissions from decay are detected. Emissions along different lines of response through the patient are counted. The detected events from different sampling locations are counted or collected. The lines of response or lines along which the different events occur are used in reconstruction. The lines of response are based on the position and/or angle of the detector and patient when the event occurred. The distribution in three dimensions of the emissions from the patient may be reconstructed from the events and corresponding lines of response.

The image processor tomographically reconstructs the activity distribution of an internal region of the patient from the sensed radiation. The lines of response and events are used to reconstruct a two or three-dimensional representation of activity in the patient. Reconstruction may be in one dimension or a value for a region or organ, such as a list of organs with corresponding activity per organ. Any SPECT reconstruction may be used. In an iterative optimization, the locations of emissions are determined from the detected signals. Tomographic reconstruction is used to reconstruct the locations of the radioisotope.

In act 32, the user or image processor selects near-field or far-field scanning for a portable solid-state detector. The portable SPECT scanner may be positioned at any of various distances from the patient to scan, depending on the environment. For example, the detector may be positioned 0.01-10 meters from the patient. Depending on the effective angle of sensing of the detector and/or collimator, the angle formed for detection may cover only part of the region of interest of the patient at a given distance. Near-field scanning is selected in this instance. Where the angle formed for detection covers all of the region of interest of the patient at the distance, then far-field scanning is selected. The selection may be different for different SPECT scans.

The selection may be based on sensing the patient, such as with a camera and determining the distance (e.g., using a depth camera). The image processor automatically determines the distance and selects. Alternatively, the user measures or estimates the distance. A user input is provided to enter the distance as a selection or to enter the selection.

For far-field scanning, the detector may be held in one position. The user or a stand holds the detector for detecting emissions from the patient. The detector may be moved about the patient to detect emissions from different directions but is not moved to detect emissions from different locations in the patient. For near-field scanning, the detector is moved to sample different locations in the patient. For any given location or group of locations, the detector may be moved to different positions to detect emissions from different directions.

In act 34, the person-carriable detector (portable scanner) is used to determine an activity distribution in the patient with a SPECT scan of the patient. The activity in the patient for a different period or time point is determined. Hours or days apart from determining activity in act 30, the portable scanner is used to determine current activity for the patient. The SPECT scan is performed to sample the activity.

The selected near-field or far-field scanning is performed to measure emissions. The user may be instructed where to move and/or position the portable scanner relative to the patient based on the near or far-field scanning. The detector may be raised, lowered, rotated, moved closer or farther away, and/or moved side-to-side to detect emissions from all of the locations of interest in the patient.

Since the fixed arrangement of bed relative to the SPECT detector is not provided with the person-carriable detector, a camera, gyroscope, accelerometer, another sensor, and/or combinations thereof are used to determine the position and orientation of the detector relative to the patient. For each emission, the line of response through the patient is determined. The position and orientation of the detector relative to the patient is found based on the camera and/or other sensors. For reconstruction, the locations (position and orientation) of the lines of response through the patient are used. The locations of the lines of response are found by the image processor using the camera and/or other sensors. For any positions and orientation of the detector in the near or far field scanning, the location of the line of response for the emission is determined to align the emission with the patient.

The image processor may use the camera and/or other sensors to align the detected emissions and/or reconstructed activities from different times. Similarly, the emissions or reconstructed activities may be aligned with imaging or coordinate system for other devices, such as aligning with camera images. The alignment may instead or also be used to align estimated or measured attenuations or anatomy structure for multi-modal reconstruction. The alignment may be for motion correction as the patient and/or scanner moves.

The image processor reconstructs a two or three-dimensional distribution of activity in the patient from the detected emissions and lines of response. Any aligned multi-modal information, such as attenuations, may be used in the reconstruction. The same or different reconstruction as performed in act 30 is used to reconstruct the activity distribution in act 34.

Since the person-carriable detector is used, the reconstructed activity distribution may have a lower spatial resolution than provided by the full-sized SPECT scanner in act 30. Where far-field scanning is used with a single orientation relative to the patient for detecting emissions, the depth resolution for a three-dimensional reconstruction may be less than the lateral resolution. Up or down sampling may be used for activity distributions of different resolutions to estimate the dose.

The reconstruction used may vary depending on the energy. Where the reconstruction is of emissions at or below 511 keV or another threshold (e.g., 400 or 600 keV), then physical collimation is used. The lines of response are based, at least in part, on the collimator, such as a multiplexed or multichannel collimator. Where the energies are at or above the threshold, then Compton imaging is performed for the reconstruction. Electronic collimation is provided in the reconstruction.

Acts 32 and 34 may be repeated. Any repetition measures the activity distribution for a different period or timepoint. For example, the patient has a daily, weekly, or other frequency of scanning appointments. The portable scanner is used to scan the patient at each appointment, providing activity distribution for each appointment. Act 30 may be repeated. A set of activities representing the patient at different times is provided.

In act 36, the image processor or another processor estimates the internal dose to the patient. The internal dose is estimated as a fit time-activity curve. Alternatively, the dose is estimated as an integral of the fit time-activity curve.

For a given location in the patient, the activity varies over time. After aligning the locations of the activity distributions from different times, the same patient location in each activity distribution is identified. The time-activity curve is fit to the activities of that location over time (i.e., for the different scan periods). For a group of locations, the time-activity curve is fit to an average or sum of the activities of the locations in each period or timepoint. The dose for a type of tissue or particular organ may be determined.

The fitting is to any number of activities. The activity from a single period may be used. The activities from two or more, such as 5-10, periods may be used for more accurate estimation of dose.

In act 38, a display displays an image. The image processor generates an image from one or more of the reconstructed representations (activity distributions) and/or estimated dose. For showing the activity distribution at a given period, an image for two-dimensional display is formed or rendered from the representation. The image may be formed by interpolation, display value (e.g., color) mapping, filtering, and/or other image processing. For gamma ray radiation, the image may represent a spatial distribution of emissions. The result may be a map of uptake in a patient. The activity distribution may be a color-coded overlay of another image, such as CT image from the scanning in act 30 and/or an optical image from the scanner used in the scanning of act 34. The image is displayed on a display screen. Alternatively, the image is printed or projected.

For showing the dose, the image of activity distribution may be annotated with a value or chart showing dose. Alternatively, the image shows the dose without showing the activity distribution.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A single photon emission computed tomography (SPECT) system comprising:

a handheld scanner comprising a solid-state detector configured to detect emissions from a patient and an imager configured to image the patient; and an image processor configured to determine internal dose from a time activity curve formed from activities of different scans at different times, the activities tomographically formed from (1) emissions detected from the patient by the solid-state detector during the different scans of the different times and (2) output of the imager, the image processor configurable to tomographically form the activities with the patient in a far-field of the solid-state detector or a near-field of the solid-state detector.

2. The SPECT system of claim 1 wherein the imager comprises a camera, and wherein the image processor is configured to form the activities where a position or positions of the handheld scanner are determined from the output of the camera, the output being optical images.

3. The SPECT system of claim 1 wherein the imager comprises a camera, and wherein the image processor is configured to form the activities as multi-modal reconstructions with the output of the camera being images used to estimate internal structure of the patient for the multi-modal reconstructions.

4. The SPECT system of claim 1 wherein the imager comprises a camera, and wherein the image processor is configured to form the activities where a position or positions of the patent at the different times are determined from the output of the camera, and the time activity curve is determined with the activities of the different times aligned with the output of the camera.

5. The SPECT system of claim 1 wherein the image processor is configured to determine the dose by fitting the time activity curve to the activities of the different times.

6. The SPECT system of claim 5 wherein the image processor is configured to determine the dose by fitting the time activity curve to the activities of the different times and an activity of an additional time, the activity of the additional time being from a SPECT scanner having a bed onto which the patient is placed for scanning.

7. The SPECT system of claim 1 wherein the handheld scanner weighs 5 kilograms or less.

8. The SPECT system of claim 1 wherein the solid-state detector is configured to detect a different energies and wherein the image processor is configurable to tomographically form using a collimator for a lower one of the different energies and using Compton imaging for a higher one of the different energies.

9. The SPECT system of claim 1 wherein the handheld scanner further comprises a gyroscope, and wherein the image processor is configured to form the activities using orientations from the gyroscope.

10. The SPECT system of claim 1 wherein far-field comprises the patient being within a subtended angle of the solid-state detector encompassing the patient such that the activity is formed with the handheld scanner in one position, and wherein near-field comprises the patient being closer to the handheld scanner wherein the subtended angle covers only a portion of the patient such that the activity is formed with the handheld scanner being moved to sense from different positions relative to the patient.

11. The SPECT system of claim 1 wherein the solid-state detector has a spatial resolution of 1 mm or less and is less than 500 square centimeters, wherein far-field is a distance from the patient to the handheld scanner of at least 1 meter.

12. The SPECT system of claim 1 further comprising a mount connectable to the handheld scanner, the handheld scanner being connected to the mount for at least one of the different scans.

13. A method for internal dose assessment in single photon emission computed tomography (SPECT), the method comprising:

determining a first activity distribution in a patient with a first SPECT scan of the patient on a bed of a SPECT scanner, the first activity distribution representing the patient at a first period;

determining a second activity distribution in the patient with a second SPECT scan of the patient using a person-carriable detector, the second activity distribution representing the patient at a second period; and estimating the internal dose to the patient from the first and second activity distributions.

14. The method of claim 13 wherein determining the first activity distribution comprises reconstructing the first activity distribution from the first SPECT scan as a multimodality scan using computed tomography, and wherein determining the second activity distribution comprises reconstructing the second activity distribution at a lower spatial resolution than the first activity distribution.

15. The method of claim 13 wherein estimating the internal dose comprise fitting a time activity curve to activities of the first and second activity distributions.

16. The method of claim 13 wherein determining the second activity distribution comprises determining by detection of emissions using the person-carriable detector being positioned at different orientations relative to the patient wherein a camera and/or gyroscope of the person-carriable detector is used to align the emissions with the patient.

17. The method of claim 13 wherein determining the second activity distribution comprises determining with a lesser depth resolution than lateral resolution and the person-carriable detector being held in a single orientation relative to the patient during the second SPECT scan.

18. The method of claim 13 wherein determining the second activity distribution comprises determining with emissions detected by the person-carriable detector at energies at or below 511 KeV and reconstruction relying on lines-of-response based, at least in part, on collimation.

19. The method of claim 13 wherein determining the second activity distribution comprises determining with emissions detected by the person-carriable detector at energies at or above 511 KeV and reconstruction with Compton imaging.

20. A method for internal dose assessment in single photon emission computed tomography (SPECT), the method comprising:

determining a first activity distribution in a patient with a first SPECT scan of the patient on a bed of a SPECT scanner, the first activity distribution representing the patient at a first period;

selecting near-field or far-field scanning for a portable solid-state detector;

determining a second activity distribution in the patient with the portable solid-state detector using the selected near-field or far-field scanning; and estimating the internal dose to the patient from the first and second activity distributions.

* * * * *